(12) United States Patent
Czerney et al.

(10) Patent No.: US 7,351,829 B2
(45) Date of Patent: Apr. 1, 2008

(54) COMPOUNDS ON THE BASIS OF 2- AND 4-CHROMENYLIDENE-MEROCYANINES RESPECTIVELY, AND THEIR USE

(75) Inventors: Peter Czerney, Weimar (DE); Wilhelm Frank, Jena (DE); Matthias Wenzel, Jena (DE); Frank Lehmann, Jena (DE)

(73) Assignee: Dyomics GmbH, Jena (DE)

( * ) Notice: Subject to any disclaimer, the term of this patent is extended or adjusted under 35 U.S.C. 154(b) by 0 days.

(21) Appl. No.: 10/190,371

(22) Filed: Jul. 3, 2002

(65) Prior Publication Data

US 2003/0045717 A1  Mar. 6, 2003

(30) Foreign Application Priority Data

Jul. 3, 2001  (DE) ................ 101 32 143
Jul. 3, 2001  (DE) ................ 101 32 144

(51) Int. Cl.
C07D 239/62 (2006.01)
C07D 239/66 (2006.01)
C09B 57/02 (2006.01)

(52) U.S. Cl. ................ 544/300; 252/301.16
(58) Field of Classification Search ............ 544/300; 252/301.16; 514/301.16

See application file for complete search history.

(56) References Cited

U.S. PATENT DOCUMENTS

| 4,956,480 A | 9/1990 | Robinson |
| 5,616,502 A | 4/1997 | Haugland et al. |
| 5,627,027 A | 5/1997 | Waggoner |
| 5,696,157 A | 12/1997 | Wang et al. |

FOREIGN PATENT DOCUMENTS

GB          2013703 A       8/1979

OTHER PUBLICATIONS

Beilstein Institut Zur Foerderung Der Chemischen Wissenschaften; Substance; Database Crossfire Beilstein "Online", XP002212813; pp. 1-2; 1959; Weinheim.
Beilstein Institut Zur Foerderung Der Chemischen Wissenschaften; Substance; Database Crossfire Beilstein "Online", XP-002212812; p. 1; 1976; Weinheim.
Rezende, et al; Merocyanine-type dyes from barbituric acid derivatives; Spectrochimica Acta. Part A 57 (2001) pp. 1183-1190; May 6, 2001; Molecular Spectroscopy, XP 008000820; Pergamon Press, Oxford, Great Britain.

Primary Examiner—Venkataraman Balasubramanian
(74) Attorney, Agent, or Firm—Andrus, Sceales, Starke & Sawall, LLP

(57) ABSTRACT

The invention relates to compounds based on merocyanines with the general formulas I and/or II,

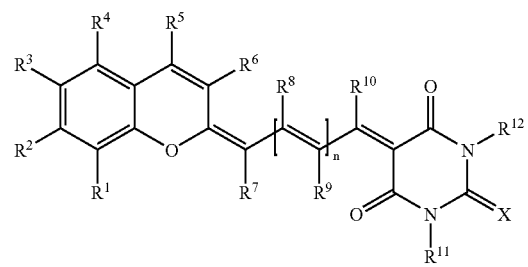

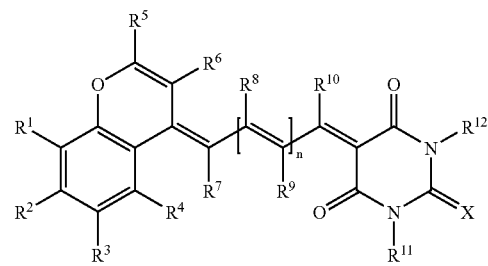

where n=0 or an integer from 1 to 3, X=O or S and the residues $R^1$ to $R^{12}$ are the same or different and signify in particular hydrogen or various organic residues, without or with functional groups, and $R^2$ incorporates an amine function.

The compounds in accordance with the invention are suitable as fluorescent dyes (fluorophores) for used in optical determination and demonstration methods, in particular those employing fluorescence, for example in medicine, pharmacology and the biological, materials and environmental sciences. They are characterized by high photostability and long storage life, and exhibit a high fluorescence quantum yield. Excitation causing them to emit light can be achieved in a simple manner, by white-light sources or by laser irradiation in the UV, visible or NIR spectral region.

6 Claims, 9 Drawing Sheets

Fig.: 1
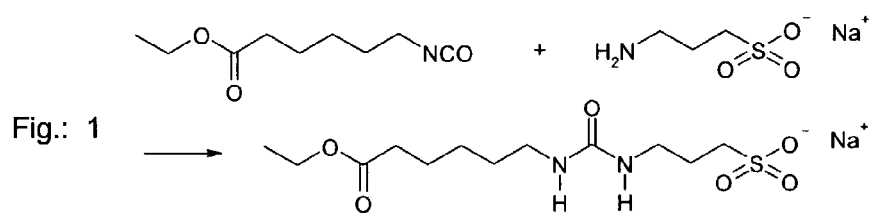
Fig.: 2
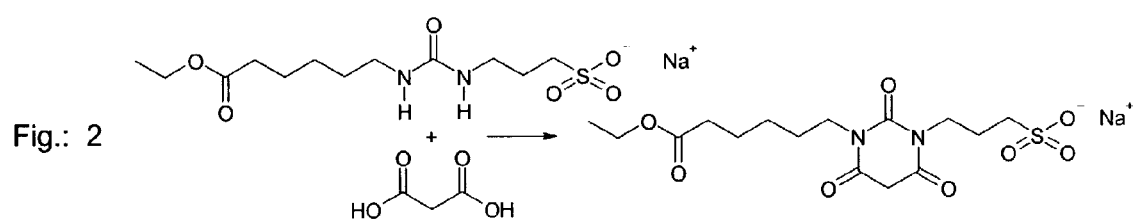
Fig.: 3
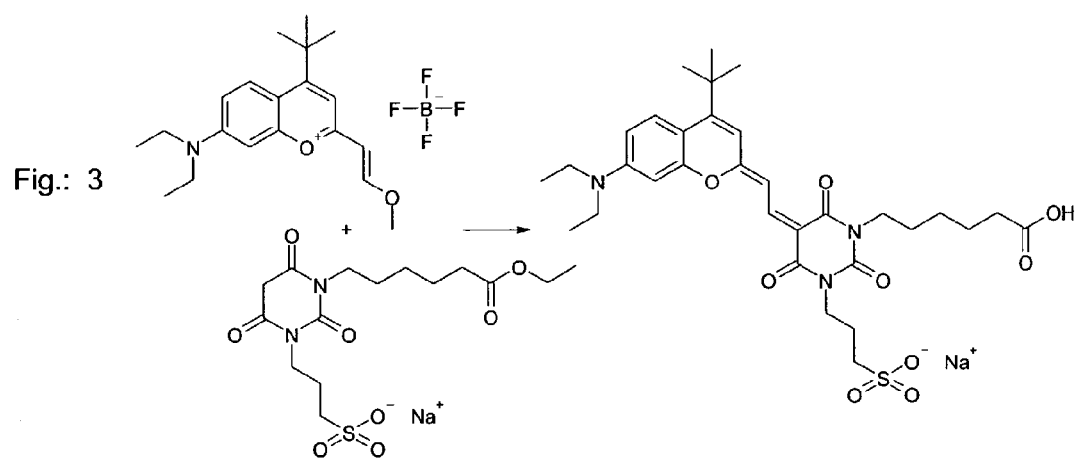

Fig.: 4
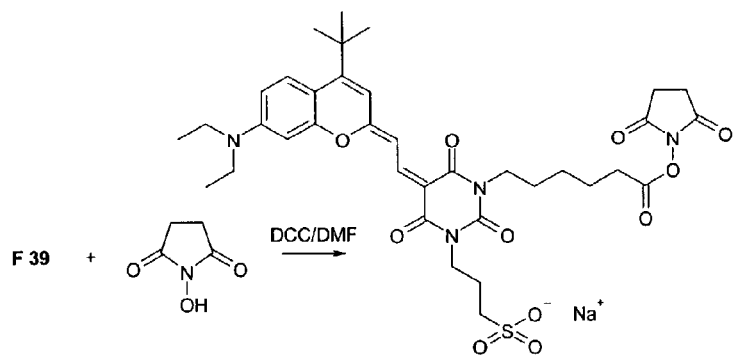
Fig.: 5
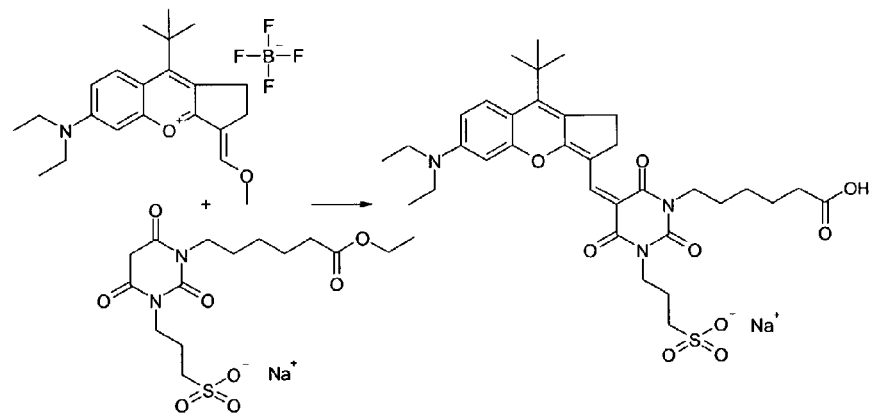

Fig.: 6
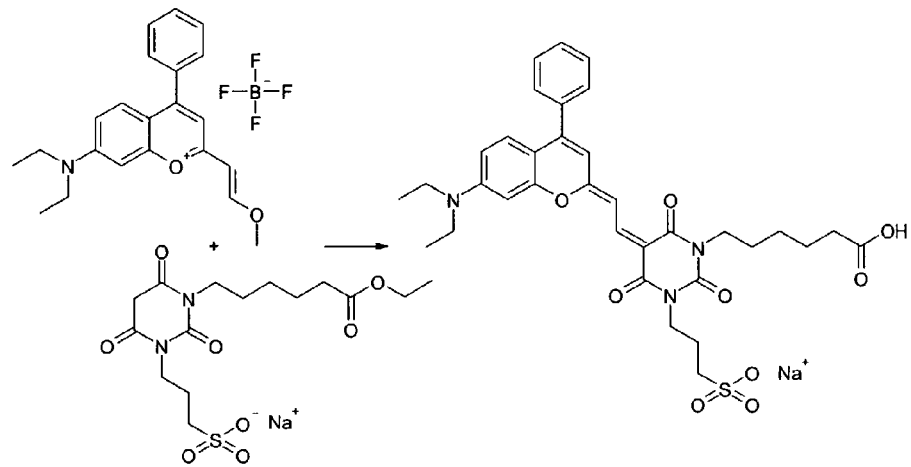
Fig.: 7
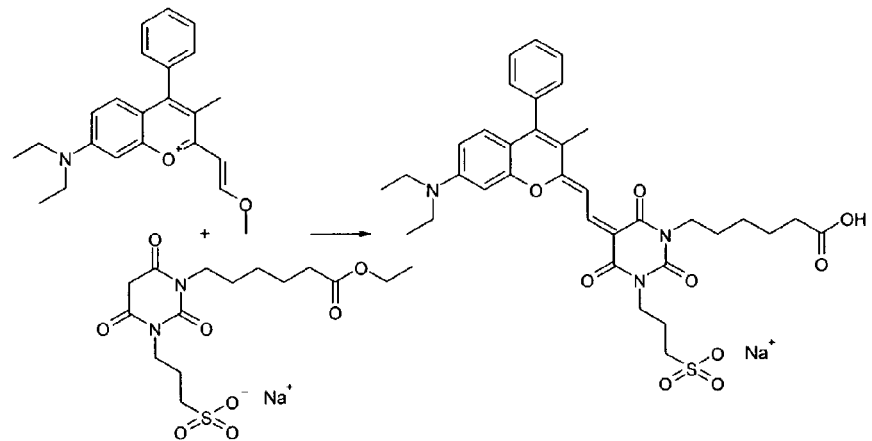

Fig.: 8
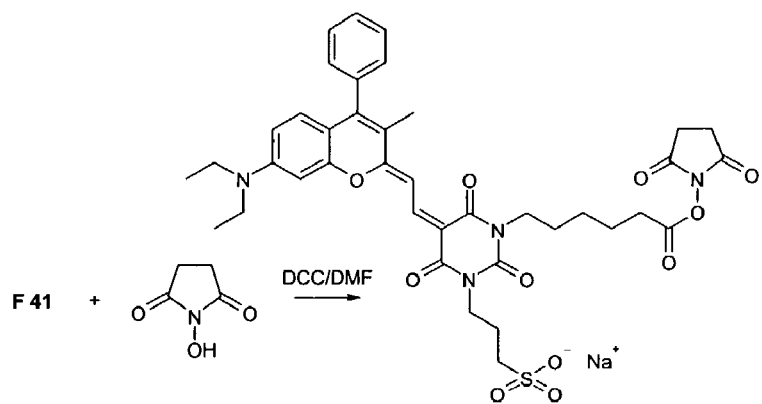
Fig.: 9
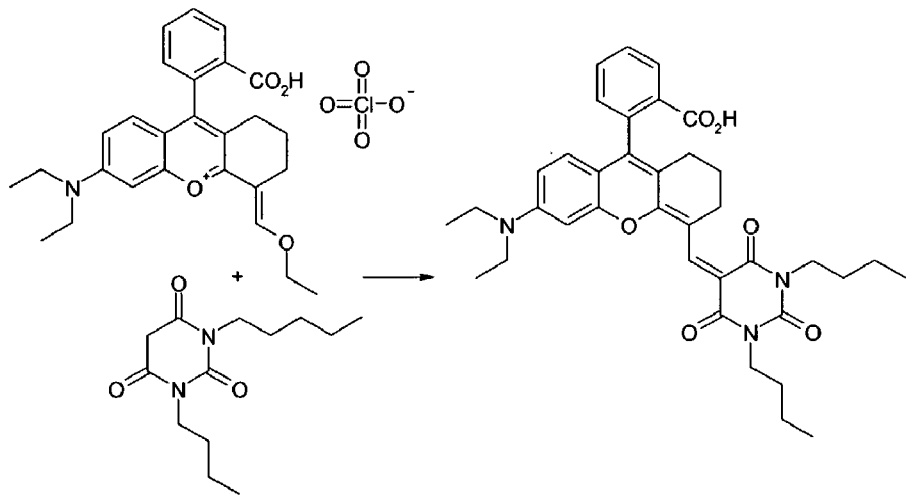
Fig.:10
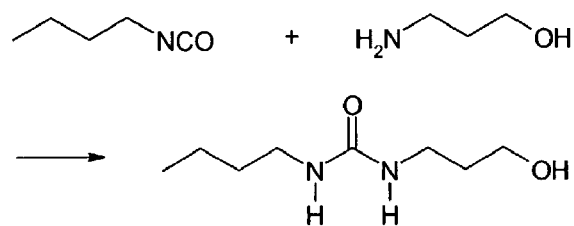

Fig.:11 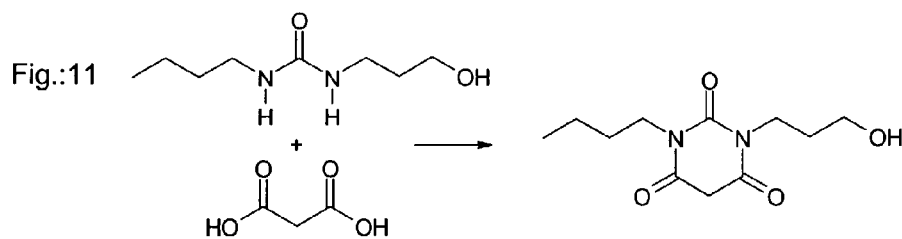
Fig.:12 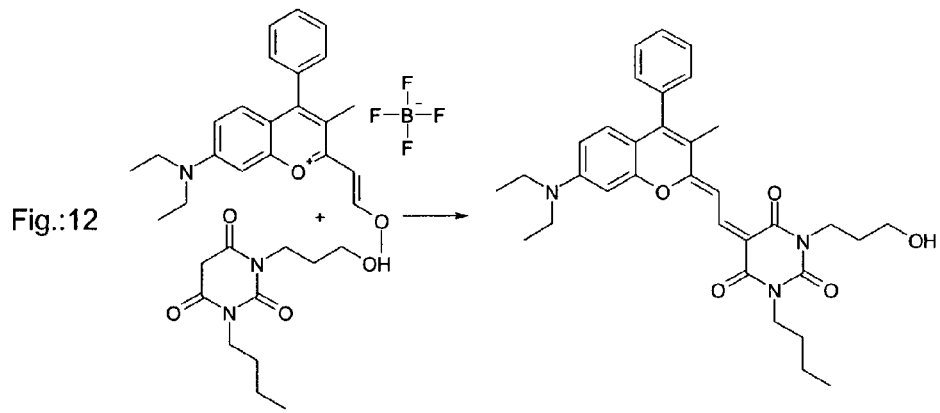
Fig.:13 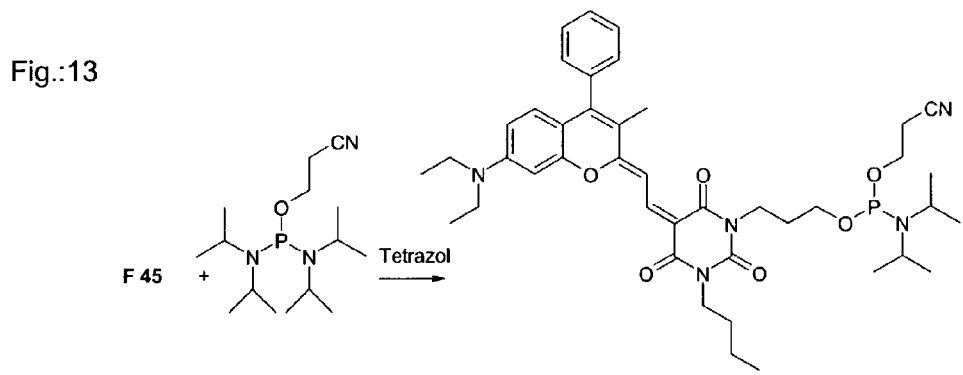

Fig.:14 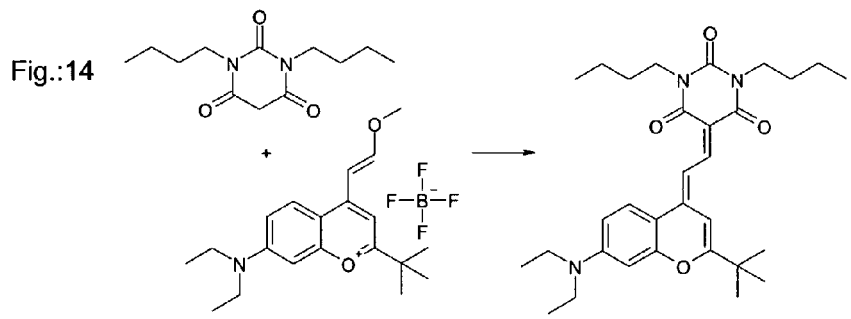
Fig.:15 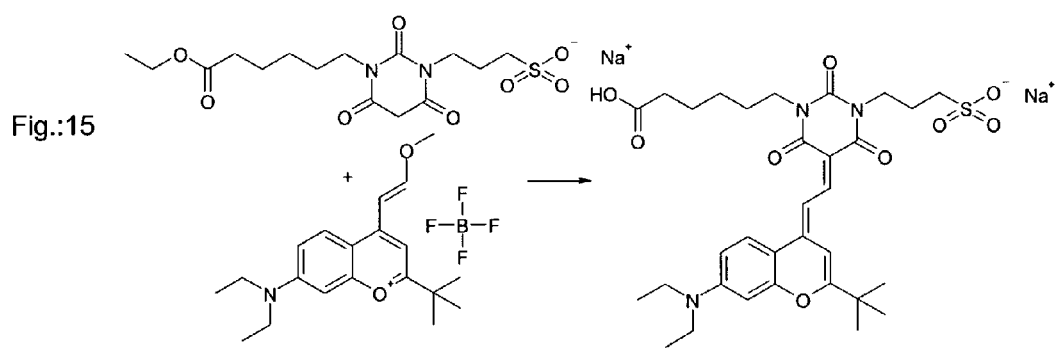
Fig.:16 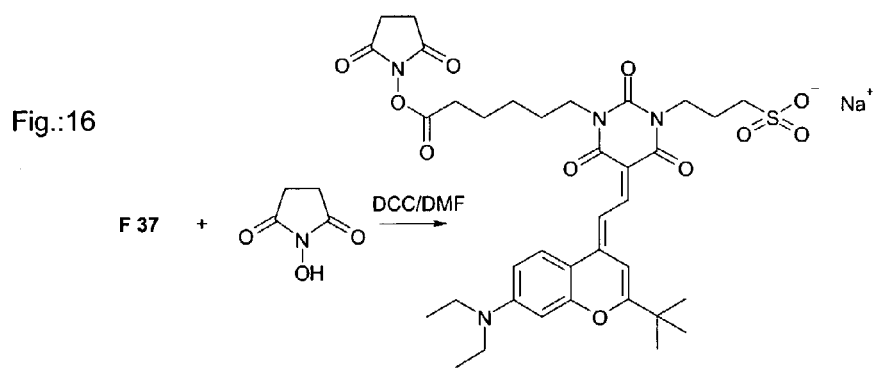
Fig.:17 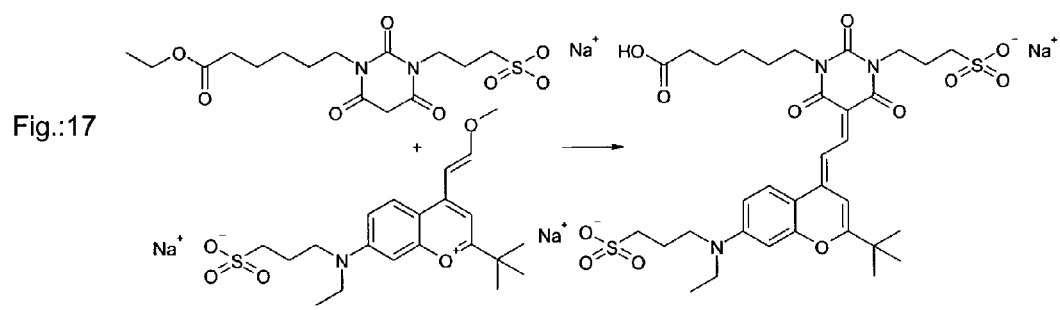

Fig.:18
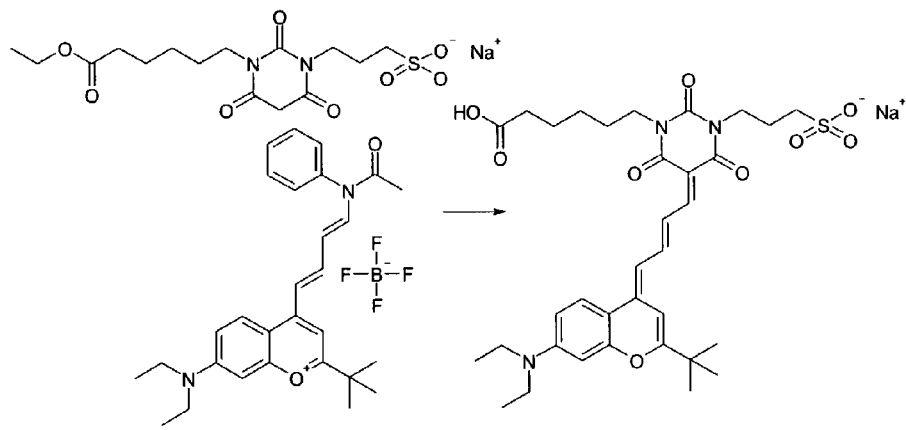
Fig.:19
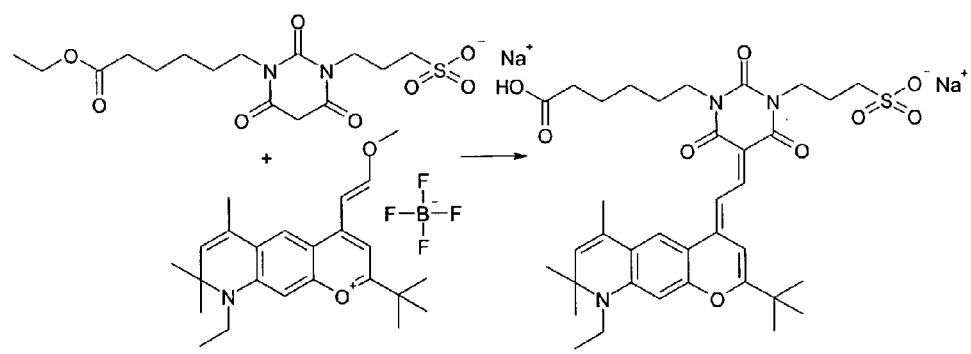
Fig.:20
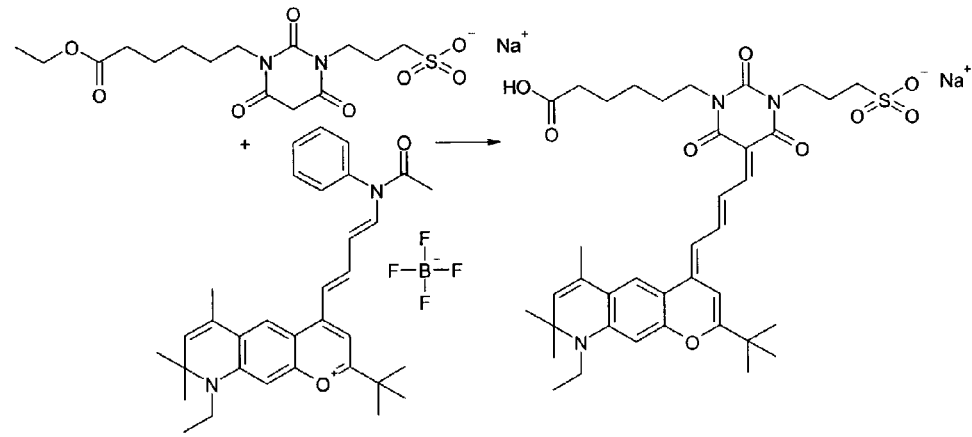

Fig.:21
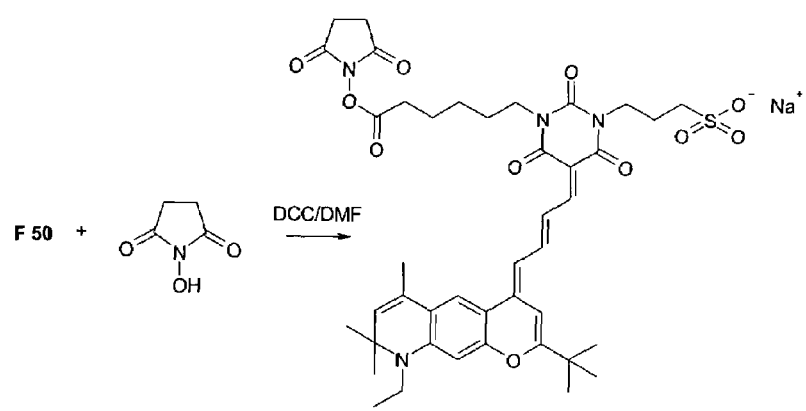
Fig.:22
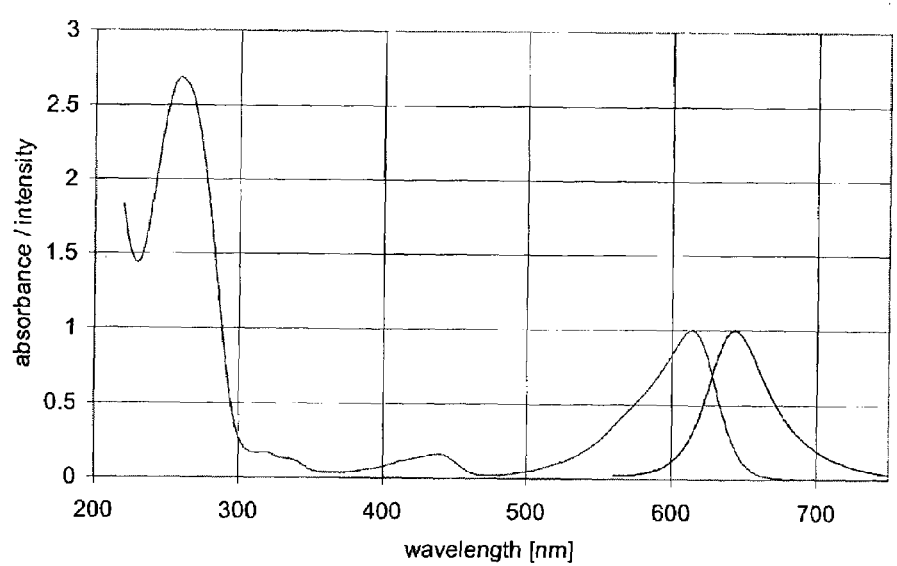

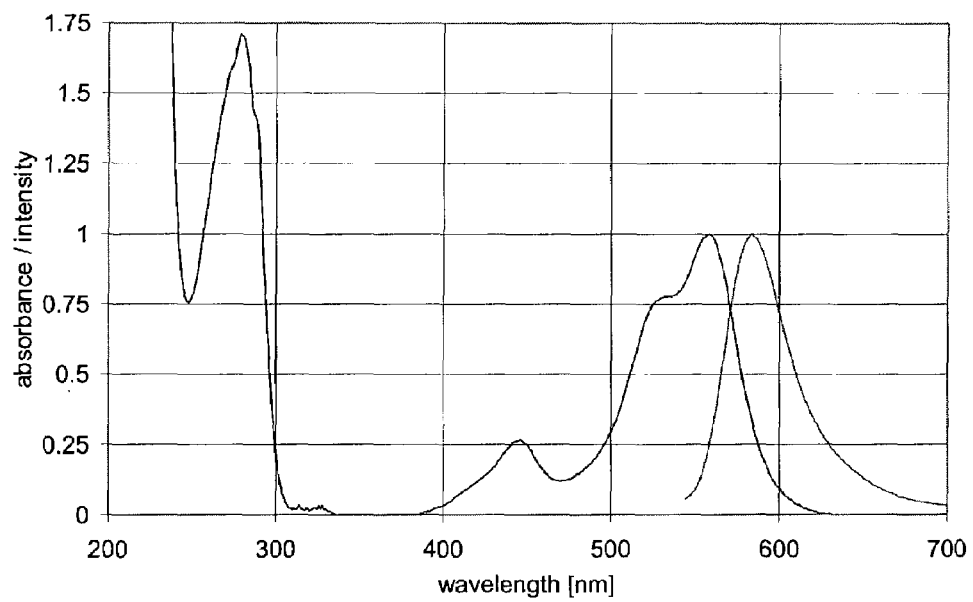
Fig.:23

COMPOUNDS ON THE BASIS OF 2- AND 4-CHROMENYLIDENE-MEROCYANINES RESPECTIVELY, AND THEIR USE

DESCRIPTION OF THE INVENTION

Compounds Based on Merocyanine Compounds and Their Use

The invention relates to compounds suitable for use as fluorescent dyes (fluorophores) that are based on merocyanines, and to their use in optical determination and demonstration procedures, in particular those involving fluorescence. Typical applications include methods employing a reaction of dye-labelled biomolecules such as antigens, antibodies or DNA segments with the corresponding complementary species. This reaction enables measurements of enzyme kinetics, receptor-ligand interactions, the kinetics of nucleic-acid hybridization etc. Furthermore, the claimed fluorophores are of interest for the pharmacological characterization of receptors or chemical agents.

Opportunities for such application arise, for example, in medicine and pharmacology, in the biological and materials sciences, in monitoring the environment and demonstrating the presence of organic and inorganic microsamples that occur in nature and technology, as well as in other areas.

Whereas cyanines have long been known as a fluorescence marker (U.S. Pat. No. 5,627,027), as yet merocyanine compounds have only occasionally been employed. Typical examples here are markers of the type AMCA (7-amino-4-methylcoumarin-3-acetic acid; U.S. Pat. No. 5,696,157 and U.S. Pat. No. 4,956,480). The characteristic feature of these compounds is that their absorption bands are in the UV region, or at the beginning of the visible spectral region. Accordingly, the emission can be observed only at wavelengths below 500 nm.

Merocyanines, e.g. Merocyanine 540, are also used to demonstrate and quantify peptides, polypeptides and proteins (U.S. Pat. No. 5,616,502). The disadvantage of the fluorescent markers claimed in U.S. Pat. No. 5,616,502 is that they offer no possibility of introducing a reactive function that enables covalent coupling to a nucleophilic biomolecule.

It is the objective of the invention to create compounds based on merocyanines that are suitable as fluorescent markers, with high photostability and long storage life as well as a high fluorescence quantum yield. In order to achieve an optimal signal-to-noise ratio, the emission bands should be in the wavelength region above 550 nm, and excitation should be achieved in the simplest possible way, by means of white light or laser irradiation in the UV, visible or near infrared spectral region. Insofar as possible, the fluorescence of the markers should be high regardless of the pH value and other factors in the surroundings. A prerequisite for covalent binding is the presence of a reactive function that reacts with the biomolecule to be labelled under physiological conditions, or under the reaction conditions customary during the solid-phase synthesis of biooligomers.

The subject matter of the invention consists of new compounds based on merocyanines with the general formulas I and II,

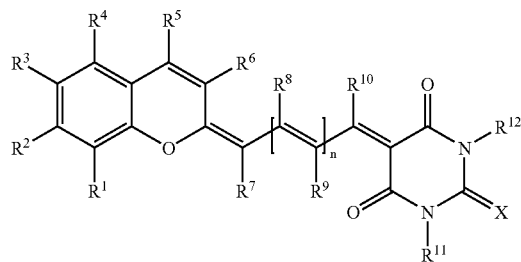

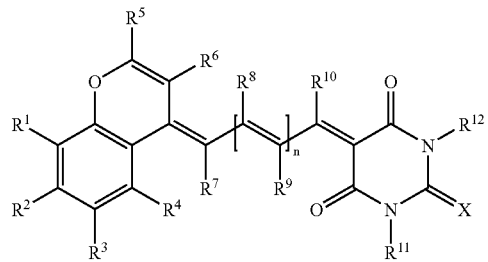

where $R^1$-$R^{12}$ are the same or different and can represent any of the following: hydrogen; one or more chlorine and/or bromine atoms; alkyl, aryl, heteroaryl, cycloalkyl, heterocycloalkyl, alkyloxy, alkylmercapto (here the terms "alkyl" and "cycloalkyl" are intended to include residues with olefin bonds), aryloxy, arylmercapto, heteroaryloxy, heretoarylmercapto or cyano residues; one or more hydroxy- and one or more alkyl-substituted or cyclic amino functions. One or more aliphatic, heteroaliphatic or aromatic rings can be formed by the following combinations: $R^1$ and $R^2$, $R^2$ and $R^3$, $R^3$ and $R^4$, $R^5$ and $R^6$ and/or $R^6$ and $R^7$, X stands for an element in the group O, S, Se, Te or the structural element $CR_2$ or NR, where R can take on the functions of $R^1$-$R^{12}$, one or more of the groups $R^1$-$R^{12}$ can be solubilizing or ionizable or ionized groups such as $SO_3^-$, $PO_3^{2-}$, $CO_2H$, OH, $NR_3^+$, cyclodextrin or sugar, which determine the hydrophilic properties of the dye; these groups can also be bound to the actual chromophore by way of an aliphatic or heteroaliphatic, or where appropriate cyclic spacer group, at least one of $R^1$-$R^{12}$ stands for a reactive group of one of the following types: isocyanate, isothiocyanate, hydrazine, amine, monochloro- and dichloro- or monobromo- and dibromotriazine, aziridine, sulfonyl halogenide, N-hydroxysuccinimide ester, imido ester, glyoxal or aldehyde, alternatively maleimide or iodacetamide, and phosphoramidite; again, the substituent in each case can be bound to the actual chromophore by way of an aliphatic or heteroaliphatic, or where appropriate cyclic spacer group, the aliphatic or heteroaliphatic spacer group consists of a structural element —[$(CH_2)_a$—Y—$(CH_2)_b$]$_c$—, where Y can be the same or different for the various substituents and has a $CR_2$—, O—, S—, $SO_2$, $SO_2NH$—, NR—, COO— or CONR— function, where R can serve the functions of $R^1$-$R^{12}$; a and b can be the same or different and represent numbers within the range 0-18, and c is within the range 1-18, n stands for the numerical value 0, 1, 2 or 3, and in the case of $R^8$ and $R^9$, where n=2 or 3, the two or three groups thus specified can be the same or different, and $CR^{10}$ stands for one of the structural units

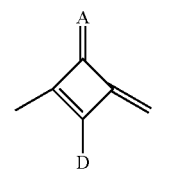

III

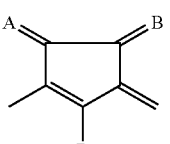

IV

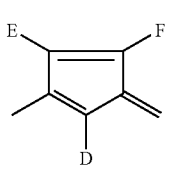

V

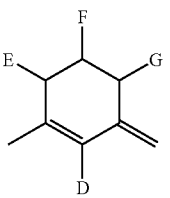

VI

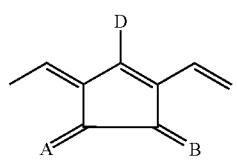

VII

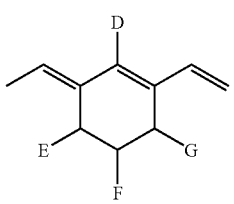

VIII where the groups A and B may be the same or different and each stand for two substituents of the type $R^1$-$R^{12}$, for $CR_2$ or N—R, where R can have the same or different functions of $R^1$-$R^{12}$, or for O or S, and the groups D-G can perform the same or different functions of $R^1$-$R^{12}$.

Typical compounds in accordance with the invention are in particular those with the formulas I and II, wherein $R^1$-$R^{12}$ are the same or different and signify hydrogen, chlorine, bromine, an aliphatic or mononuclear aromatic residue, in each case with a total of at most 12, preferably at most 10, in particular at most 8 carbon atoms, which as a substituted residue can also contain, apart from carbon and hydrogen, as many as 4 oxygen atoms and 0, 1 or 2 nitrogen atoms or one sulfur atom or one sulfur and one nitrogen atom, or represent an amine function with a nitrogen atom to which are bound hydrogen or substituents with a total of at most 8 carbon atoms, such that these substituents consist of carbon, hydrogen and at most two sulfonic acid groups; here $R^1$ and $R^2$, $R^2$ and $R^3$, $R^3$ and $R^4$, $R^5$ and $R^6$, and $R^6$ and $R^7$ each together can form an aromatic or non-aromatic carbohydrate- or nitrogen-containing 5- or 6-membered ring, the crucial aspect being that $R^2$ represents an amine function and that at least one of the residues $R^1$ and $R^3$ can independently represent an $SO_3^-$ residue, X represents oxygen or sulfur, oxygen being preferred, and n=0 or an integer from 1 to 3, and the substituents $R^8$ and $R^9$, which in the case of n=2 or 3 are present doubly or triply, can be the same or different, although n is preferably 0 or 1.

A special group of compounds in accordance with the invention includes those in which $R^2$, $R^{11}$ and $R^{12}$ are free of chlorine and bromine but at most 4, advantageously at most 2 of the residues $R^1$ and $R^3$ to $R^{10}$ do contain chlorine and/or bromine. It is preferred for all residues $R^1$ and $R^3$-$R^{10}$ to be free of chlorine and bromine.

Some preferred compounds contain aliphatic residues $R^1$-$R^{12}$ with 2-6 carbon atoms substituted in the ω position by a reactive group, e.g. $SO_3^-$, $SO_2Cl$—, HO—, or carboxyl, which in turn can be converted to esters, e.g. with N-hydroxysuccinimide, maleimide or phosphoramidite, or also with the above-mentioned reactive groups of the isocyanate type and the like. Such groups cause the compounds in accordance with the invention to be capable of reacting with biomolecules by forming a covalent bond.

Particularly suitable compounds are those in which the residues $R^1$ to $R^{12}$ apart from the amine function of $R^2$ contain a total of maximally 2 nitrogen atoms.

Insofar as residues $R^1$ to $R^{12}$ are carbohydrates, those with 1-4 carbon atoms are preferred.

In one group of preferred compounds at least one of the residues $R^1$ to $R^{12}$ contains a solubilizing or ionizable group, which preferably is bound to the skeletal structure by way of an aliphatic or heteroaliphatic group. The term "ionizable" is understood also to include "ionized". Such solubilizing or ionizable groups are in particular $SO_3^-$, $CO_2H$ or OH, as well as $PO_3^{2-}$, $NR_3^+$, cyclodextrin or sugar. Such groups endow the compounds in accordance with the invention with additional hydrophilic properties, which have a positive effect on the fluorescence quantum yield in particular.

The compounds in accordance with the invention can be used as dyes for the optical marking of proteins, nucleic acids, oligomers, DNA, RNA, biological cells, lipids, mono-, oligo- and polysaccharides, ligands, receptors, polymers, drugs or polymer particles; also, as dyes in systems for the qualitative or quantitative determination of proteins, nucleic acids, oligomers, DNA, RNA, biological cells, lipids, polymers, drugs or polymer particles, they can be coupled to a HO—, $H_2N$—, HS— or $HO_2C$-function of the substances of interest by way of the functional groups.

This coupling reaction is advantageously carried out in organic or aqueous solutions.

The conjugates comprising the compounds in accordance with the invention and biomolecules have fluorescent properties.

The compounds in accordance with the invention find employment in optical qualitative or quantitative determination methods, in particular those based on fluorescence, that include immune tests, hybridization procedures, chromatographic or electrophoretic methods and high-throughput screenings or analysis of receptor-ligand interactions on a microarray.

The merocyanines having the general formulas I and/or II can be used as dyes for optical labeling of organic or inorganic identification units such as amino acids, peptides, proteins, antigens, haptens, enzyme substrates, enzyme cofactors, biotin, carotenoids, hormones, neurohormones, neurotransmitters, growth factors, lympholocines, lectins, toxins, carbohydrates, oligosaccharides, polysaccharides, dextrans, nucleic acids, oligonucleotides, DNA, RNA, biological cells, lipids, receptor-binding drugs or organic or inorganic polymeric carrier materials.

Labeling of the identification units can be accomplished by inducing ionic interactions between the compounds with the general formulas I and/or II and the materials to be labeled.

It is also possible to bind the identification unit or the carrier material covalently to the fluorophore. This coupling reaction can be carried out in aqueous or predominantly aqueous solution and preferably at room temperature. In the process a fluorescent probe (conjugate) is produced for the qualitative or quantitative determination of various biomaterials or other organic and inorganic materials.

Both the compounds with the general formulas I and/or II and systems derived therefrom can be employed in optical qualitative and quantitative determination methods, in particular those based on fluorescence, for the diagnosis of cell properties, in biosensors (point-of-care measurements), for research on the genome and in miniaturization technologies. Typical applications are found in the areas of cytometry and cell sorting, fluorescence correlation spectroscopy (FCS), in ultra-high-throughput screening (UHTS), in multicolor fluorescence in situ hybridization (FISH) and in microarrays (DNA and protein chips).

Such a microarray is a raster-like arrangement of molecules immobilized on at least one surface, which can be used for studying receptor-ligand interactions. The term "raster-like arrangement" signifies more than two molecules, different from one another, which are situated within an area and are immobilized there in different, previously specified regions with known positions.

A receptor is a molecule that has an affinity for a given ligand. Receptors can be either naturally occurring or artificially produced molecules. Receptors can be employed in pure form or bound to other species. Receptors can be bound to a binding partner covalently or not covalently, either directly or by way of particular coupling mediators.

Examples of receptors that can be detected by means of this invention include agonists and antagonists for cell-membrane receptors, toxins and other poisons, viral epitopes, hormones such as opiates and steroids, hormone receptors, peptides, enzymes, enzyme substrates, agents acting as cofactors, lectins, sugar, oligonucleotides, nucleic acids, oligosaccharides, cells, cell fragments, tissue fragments, proteins and antibodies, but are not restricted to the substances mentioned here.

A ligand is a molecule that is recognized by a particular receptor. Examples of ligands that can be detected by the compounds in accordance with the invention include agonists and antagonists for cell-membrane receptors, toxins and other poisons, viral epitopes, hormones such as opiates and steroids, hormone receptors, peptides, enzymes, enzyme substrates, agents acting as cofactors, lectins, sugar, oligonucleotides, nucleic acids, oligosaccharides, cells, cell fragments, tissue fragments, proteins and antibodies, but are not restricted to the substances mentioned here.

By the preparation of non-symmetric merocyanines, which comprise on one hand, as terminal function, an easily derivatizable heterocycle of the type CH-acid compounds, and on the other hand a 6-membered ring heterocycle with novel substituents, the following advantages in particular are achieved.

Even relatively small molecules absorb in the spectral region above 550 nm and in comparison to the previously known polymethines with absorption maxima above 650 nm (penta- and heptamethines) have substantially improved photochemical and thermal stability.

Molecular engineering makes it possible to control the position and intensity of the absorption and emission maxima as desired and adapt them to the emission wavelengths of various excitation lasers, especially diode lasers.

Depending on the choice of suitable terminal heterocycles, the dyes in accordance with the invention exhibit additional absorption maxima in the visible or NIR spectral region that can be used for excitation, for instance with an argon laser. These dyes are well suited in particular for use in multiple color fluorescence assays.

The compounds in accordance with the invention are relatively simple to manufacture, by condensation of the two different CH-acidic heterocycles and a C-1, C-3 or C-5 component (single-vessel method).

Other methods of producing them consist of more than one reaction step; in a first step one of the CH-acidic heterocycles is condensed with the C-1, C-3 or C-5 component and after isolation of the 1:1 condensation product, the latter is converted to merocyanine in a subsequent condensation with the second CH-acidic heterocycle. The sequence in which the heterocycles react is unimportant here. The result is that in a few reaction steps a large number of variously functionalized dyes, which differ with respect to the overall charge and the specificity/reactivity of the activated groups used for immobilization, can be produced in a simple manner.

A further objective of the invention is the employment of the compounds in accordance with the invention as dye components for the optical labeling of biological and organic substances such as proteins, nucleic acids and the other substances mentioned above.

The compounds in accordance with the invention are suitable for use as fluorescent dyes (fluorophores) in optical determination and demonstration methods, in particular those based on fluorescence, for example in medicine, pharmacology and the biological, materials and environmental sciences. They are characterized by high photostability and long storage life, and have a high fluorescence quantum yield. They can be excited in a simple manner by white-light sources or by laser irradiation in the UV, visible or NIR spectral region.

In the following the invention is explained with reference to exemplary embodiments represented in the drawings, wherein FIG. 1 shows the synthesis of the sodium salt of N-(5-ethoxycarbonyl)-pentyl-N'-3-sulfonatopropyl urea, preliminary product A FIG. 2 shows the synthesis of the sodium salt of 1-N-(5'-ethoxycarbonyl)-pentyl-3-N'-3'-sulfonatopropyl-2,4,6-trioxo-5H-pyrimidine, preliminary product B FIG. 3 shows the synthesis of the sodium salt of 3-[5-{2-[4-(tert-butyl)-7-(diethylamino)-2H-2-chromenylidene]ethylidene}-3-(5-carboxypentyl)-2,4,6-trioxohexahydro-1-pyrimidinyl]-1-propane sulfonate (F 39/DY-610), exemplary embodiment 1

FIG. 4 shows the synthesis of the N-hydroxysuccinimide ester (NHS) of F 39, exemplary embodiment 2

FIG. 5 shows the synthesis of the sodium salt of 3-[5-{[9-(tert-butyl)-6-(diethylamino)-1,2-dihydrocyclopenta[b]

chromen-3-yl]methylene}-3-(5-carboxypentyl)-2,4,6-tri-oxohexahydro-1-pyrimidinyl]-1-propane sulfonate (F 46), exemplary embodiment 3

FIG. 6 shows the synthesis of the sodium salt of 3-[5-{2-[4-(phenyl)-7-(diethylamino)-2H-2-chromenylidene]ethylidene}-3-(5-carboxypentyl)-2,4,6-trioxohexahydro-1-pyrimidinyl]-1-propane sulfonate (F 40), exemplary embodiment 4

FIG. 7 shows the synthesis of the sodium salt of 3-[5-{2-[3-(methyl)-4-(phenyl)-7-(diethylamino)-2H-2-chromenylidene]ethylidene}-3-(5-carboxypentyl)-2,4,6-trioxohexahydro-1-pyrimidinyl]-1-propane sulfonate (F 41), exemplary embodiment 5

FIG. 8 shows the synthesis of the NHS ester of F 41, exemplary embodiment 6

FIG. 9 shows the synthesis of 1,3-dibutyl-5-{[9-(2-carboxyphenyl)-6-(diethylamino)-2,3-dihydro-1H-4-xanthenyl]methylene}-hexahydro-2,4,6-pyrimidine trione (F 33), exemplary embodiment 7

FIG. 10 shows the synthesis of N-(3-hydroxypropyl)-N'-butyl urea, preliminary product C FIG. 11 shows the synthesis of 1-N-(3'-hydroxypropyl)-3-N'-butyl-2,4,6-trioxo-5H-pyrimidine, preliminary product D FIG. 12 shows the synthesis of 1-butyl-5-{2-[3-(methyl)-4-(phenyl)-7-(diethylamino)-2H-2-chromenylidene]ethylidene}-3-(3-hydroxypropyl)hexahydro-2,4,6-pyrimidine trione (F 45), exemplary embodiment 8

FIG. 13 shows the synthesis of the phosphoramidite of F 45, exemplary embodiment 9

FIG. 14 shows the synthesis of 1,3-dibutyl-5-{2-[2-(tert-butyl)-7-(diethylamino)-4H-4-chromenylidene]ethylidene}-hexahydro-2,4,6-pyrimidine trione (F 34), exemplary embodiment 10

FIG. 15 shows the synthesis of the sodium salt of 3-[5-{2-[2-(tert-butyl)-7-(diethylamino)-4H-4-chromenylidene]ethylidene}-3-(5-carboxypentyl)-2,4,6-trioxohexahydro-1-pyrimidinyl]-1-propane sulfonate (F 37/DY-550), exemplary embodiment 11

FIG. 16 shows the synthesis of the NHS ester of F 37, exemplary embodiment 12

FIG. 17 shows the synthesis of the disodium salt of 3-[5-(2-{2-tert-butyl-7-[ethyl-(3-sulfonatopropyl)-amino]-4H-4-chromenylidene}-ethylidene)-3-(5-carboxypentyl)-2,4,6-trioxohexahydro-1-pyrimidinyl]-1-propane sulfonate (V03-01173), exemplary embodiment 13

FIG. 18 shows the synthesis of the sodium salt of 3-[5-{(E)-4-[2-(tert-butyl)-7-(diethylamino)-4H-4-chromenylidene]-2-butenylidene}-3-(5-carboxypentyl)-2,4,6-trioxohexahydro-1-pyrimidinyl]-1-propane sulfonate (F 38), exemplary embodiment 14

FIG. 19 shows the synthesis of the sodium salt of 3-[5-{2-[2-(tert-butyl)-9-ethyl-6,8,8-trimethyl-8,9-dihydro-4H-pyrano-[3,2-g]quinolin-4-ylidene]ethylidene}-3-(5-carboxypentyl)-2,4,6-trioxohexahydro-1-pyrimidinyl]-1-propane sulfonate (F 48), exemplary embodiment 15

FIG. 20 shows the synthesis of the sodium salt of 3-[5-{4-[2-(tert-butyl)-9-ethyl-6,8,8-trimethyl-8,9-dihydro-4H-pyrano-[3,2-g]quinolin-4-ylidene]-2-butenylidene}-3-(5-carboxypentyl)-2,4,6-trioxohexahydro-1-pyrimidinyl]-1-propane sulfonate (F 50), exemplary embodiment 16

FIG. 21 shows the synthesis of the NHS ester of F 50, exemplary embodiment 17

FIG. 22 shows the absorption and emission spectrum of a DY-610-DNA conjugate, produced by NHS coupling to the 5'-aminomodified oligomer with subsequent high-pressure liquid chromatography (HPLC) purification, measured in distilled water, exemplary embodiment 18

FIG. 23 shows the absorption and emission spectrum of a DY-550-avidin conjugate, produced by NHS-ester coupling in bicarbonate buffer at pH 9.0 with subsequent purification by way of Sephadex G25 medium (eluent phosphate buffer, 22 mM, pH 7.2), exemplary embodiment 19

In the following, the term "vacuum" refers to the pressure range 30-150 mbar. The mixing ratios of liquids are volume ratios. RT signifies room temperature.

Production of the Preliminary Products A and B

A. Sodium salt of N-(5-ethoxycarbonyl)-pentyl-N'-3-sulfonatopropyl urea, cf. FIG. 1: 696 mg (5.0 mmol) 3-aminopropanesulfonic acid is dissolved in 2 ml water with the addition of 200 mg (5.0 mmol) NaOH. After dilution with 1 ml ethanol, 1315 mg (7.1 mmol) 6-isocyanatohexaneic acid ethyl ester is added in portions while stirring, in which process the temperature rises to about 40° C. Subsequently the temperature is kept at 70° C. for 10 minutes. After cooling the solvent mixture is drawn off in vacuum and the colorless residue is extracted by boiling in acetone. The fraction insoluble in acetone is filtered out, washed with warm acetone and dried. 1.52 g (88%) yield. —$^1$H NMR (250 MHz, $D_2O$): 1.21 (t, 3H), 1.29 (m, 2H), 1.43 (m,2H), 1.58 (m, 2H), 1.86 (m, 2H), 2.34 (t, 2H), 2.88 (m, 2H), 3.05 (t, 2H), 3.18 (t,2H), 4.12 (q, 2H). –MS (ESI$^\ominus$): 323 ($M^\ominus$). —$C_{12}H_{23}NaN_2O_6S$ (346.37).

B. Sodium salt of 1-A-(5'-ethoxycarbonyl)-pentyl-3-N'-3'-sulfonatopropyl-2,4,6-trioxo-5H-pyrimidine, cf. FIG. 2:

1473 mg (4.25 mmol) sodium salt of N-(5-ethoxycarbonyl)-pentyl-N'-3-sulfonatopropyl urea and 468 mg (4.5 mmol) malonic acid are dissolved in 4 ml acetic acid and warmed to 60° C. Then 8 ml acetic acid anhydride is dripped slowly into the solution and the solution is kept at 100° C. for 6 hours. After it has cooled to room temperature the solvent is removed in vacuum and ethanol is added to the residue. The resulting precipitate is removed by suction and purified by recrystallization from ethanol. 1.32 g (75%) yield. —$^1$H NMR (250 MHz, $D_2O$): 1.13 (t, 3H), 1.22 (m, 2H), 1.53 (m,4H), 1.92 (m, 2H), 2.26 (m, 2H), 2.54 (s, 2H), 2.83 (t, 2H), 3.71 (m, 2H), 3.85 (m,2H), 4.03 (q, 2H). –MS (ESI$^\ominus$): 391 ($M^\ominus$). —$C_{15}H_{23}NaN_2O_8S$ (414.40).

Exemplary embodiments 1-7 (compounds with the general formula I)

1. Sodium Salt of 3-[5-{2-[4-(tert-butyl)-7-(diethylamino)-2H-2-chromenylidene]ethylidene}-3-(5-carboxypentyl)-2,4,6-trioxohexahydro-1-pyrimidinyl]-1-propane sulfonate (F 39/DY-610), cf. FIG. 3:

Variant A 241 mg (0.60 mmol) 4-(tert-butyl)-7-(diethylamino)-2-[(E)-2-methoxy-1-ethenyl]-chromenium tetrafluoroborate and 249 mg (0.60 mmol) sodium salt of 1-N-(5'-ethoxycarbonyl)-pentyl-3-N'-3'sulfonatopropyl-2,4,6-trioxo-5H-pyrimidine are dissolved in 20 ml ethanol, ca. 1 ml trimethylamine is added and the mixture is warmed briefly to about 70° C. After cooling to room temperature it is left for 30 minutes; then the solvent is removed in vacuum and the residue chromatographed ($SiO_2$, eluent toluol/ethanol in the ratio 7:3).

The isolated ester is boiled for 2 hours with reflux in a mixture of 10 ml acetone and 10 ml 2 M hydrochloric acid, the cooled reaction solution is neutralizd with NaHCO3 and the solvent is removed in vacuum. The methanol-soluble residue is again chromatographed ($SiO_2$ RP 18, eluent methanol/water in the ratio 6:4).

170 mg (42%) yield. UV/Vis (ethanol): $\lambda_{max}$ ($\epsilon$)=609 nm (190,000 $I·mol^{-1}·cm^{-1}$) —Fluorescence (ethanol): $\lambda_{em}$=629 nm. —$^1$H NMR (250 MHz, D$_2$O): 1.00 (t, 6H), 1.25 (m, 2H), 1.27 (s, 9H), 1.43 (m, 4H), 1.87 (m, 2H), 2.08 (t, 2H), 2.79 (t, 2H), 3.20 (s, br, 4H), 3.55 (s, br, 2H), 3.71 (s, br, 2H), 6.26 (m, 2H), 6.45 (d,1H), 6.58 (d,1H), 7.70 (d,1H), 7.79 (d,1H). –MS (ESI$^\ominus$): 644 (M$^\ominus$), 322 (M–H)$^{2\ominus}$.—C$_{32}$H$_{42}$NaN$_3$O$_9$S (667.74).

Variant B 216 mg (0.60 mmol) 4-(tert-butyl)-7-(diethylamino)-2-methylchromenium tetrafluoroborate and 274 mg (0.60 mmol) sodium salt of 1-N-(5'-ethoxycarbonyl)-pentyl-5-(methoxymethylene)-3-N'-3'-sulfonatopropyl-2,4,6-trioxohexahydro-1-pyrimidine are dissolved in 20 ml ethanol, ca. 1 ml triethylamine is added and the mixture is warmed briefly to about 70° C. The reaction solution is then processed further as for Variant A.

Variant C 216 mg (0.60 mmol) 4-(tert-butyl)-7-(diethylamino)-2-methylchromenium tetrafluoroborate, 249 mg (0.60 mmol) sodium salt of 1-N-(5'-ethoxycarbonyl)-pentyl-3-N'-3'-sulfonatopropyl-2,4,6-trioxo-5H-pyrimidine, 1 ml trimethoxymethane and 1 ml pyridine are dissolved in 10 ml acetic acid anhydride and heated for 1 hour with reflux. The reaction solution is then processed further as for Variant A.

2. Preparation of the NHS Ester of F 39 with N-hydroxysuccinimide (NHS)/N,N'-dicyclohexylcarbodiimide (DCC), cf. FIG. 4:

15 mg F 39, 14 mg DCC and 4 mg NHS are dissolved in 1 ml dry DMF. Then 10 µl triethylamine is added. The reaction mixture is stirred for 24 hours at room temperature and then filtered. Subsequently the solvent is extracted and the residue washed with diethyl ether. This reaction proceeds quantitatively.

3. Sodium Salt of 3-[5-{[9-(tert-butyl)-6-(diethylamino)-1,2-dihydrocyclopenta[b]chromen-3-yl]methylene}-3-(5-carboxypentyl)-2,4,6-trioxohexahydro-1-pyrimidinyl]-1-propane sulfonate (F 46), cf. FIG. 5:

256 mg (0.60 mmol) 9-(tert-butyl)-6-(diethylamino)-3-[(E)-1-methoxymethylidene]-1H,2H,3H-cyclopenta[b]chromenium tetrafluoroborate and 249 mg (0.60 mmol) sodium salt of 1-N-(5'-ethoxycarbonyl)-pentyl-3-N'-3'-sulfonatopropyl-2,4,6-trioxo-5H-pyrimidine are brought to reaction and processed further as for exemplary embodiment 1, Variant A.

158 mg (38%) yield. UV/Vis (ethanol): $\lambda_{max}$ ($\epsilon$)=644 nm (45,700 I·mol$^{-1}$·cm$^{-1}$). —Fluorescence (ethanol): $\lambda_{em}$=670 nm. –MS (ESI$^\ominus$): 670 (M$^\ominus$), 335 (M–H)$^{2\ominus}$. —C$_{34}$H$_{44}$NaN$_3$O$_9$S (693.78).

4. Sodium Salt of 3-[5-{2-[4-(phenyl)-7-(diethylamino)-2H-2-chromenylidene]ethylidene}-3-(5-carboxypentyl)-2,4,6-trioxohexahydro-1-pyrimidinyl]-1-propane sulfonate (F 40), cf. FIG. 6:

253 mg (0.60 mmol) 4-(phenyl)-7-(diethylamino)-2-[(E)-2-methoxy-1-ethenyl]chromenium tetrafluoroborate and 249 mg (0.60 mmol) sodium salt of 1-N-(5'-ethoxycarbonyl)-pentyl-3-N'-3'-sulfonatopropyl-2,4,6-trioxo-5H-pyrimidine are brought to reaction and processed further as for exemplary embodiment 1, Variant A.

162 mg (39%) yield. UV/Vis (ethanol): $\lambda_{max}$ ($\epsilon$)=629 nm (78,400 I·mol$^{-1}$·cm$^{-1}$). –Fluorescence (ethanol): $\lambda_{em}$=670 nm. –MS (ESI$^\ominus$): 664 (M$^\ominus$), 332 (M–H)$^{2\ominus}$. —C$_{34}$H$_{38}$NaN$_3$O$_9$S (687.73).

5. Sodium Salt of 3-[5-{2-[3-(methyl)-4-(phenyl)-7-(diethylamino)-2H-2-chromenylidene]-ethylidene}-3-(5-carboxypentyl)-2,4,6-trioxohexahydro-1-pyrimidinyl]-1-propane sulfonate (F 41), cf. FIG. 7:

261 mg (0.60 mmol) 3-(methyl)-4-(phenyl)-7-(diethylamino)-2-[(E)-2-methoxy-1-ethenyl]-chromenium tetrafluoroborate and 249 mg (0.60 mmol) sodium salt of 1-N-(5'-ethoxycarbonyl)-pentyl-3-N'-3'-sulfonatopropyl-2,4,6-trioxo-5H-pyrimidine are brought to reaction and processed further as for exemplary embodiment 1, Variant A.

185 mg (44%) yield. UV/Vis (ethanol): $\lambda_{max}$ ($\epsilon$)=620 nm (64,900 I·mol$^{-1}$·cm$^{-1}$). –Fluorescence (ethanol): $\lambda_{em}$=652 nm. –MS (ESI$^\ominus$): 678 (M$^\ominus$), 339 (M–H)$^{2\ominus}$. -C$_{35}$H$_{40}$NaN$_3$O$_9$S (701.76).

6. Preparation of the NHS Ester of F 41 with N-hydroxysuccinimide (NHS)/N,N'-dicyclohexylcarbodiimide (DCC), cf. FIG. 8:

15 mg F 41, 14 mg DCC and 4 mg NHS are dissolved in 1 ml dry DMF. Then 10 µl triethylamine is added. The reaction mixture is stirred for 24 hours at room temperature and then filtered. Subsequently the solvent is extracted and the residue washed with ether. This reaction proceeds quantitatively.

7. 1,3-dibutyl-5-{[9-(2-carboxyphenyl)-6-(diethylamino)-2,3-dihydro-1H-4-xanthenyl]-methylene}-hexahydro-2,4,6-pyrimidine trione (F 33), cf. FIG. 9:

158 mg (0.66 mmol) 1-N,3-N'-dibutyl-2,4,6-trioxo-5H-pyrimidine and 351 mg (0.66 mmol) 9-(2-carboxyphenyl)-6-(diethylamino)-4-[(E)-1-ethoxymethylidene]-1H,2H,3H,4H-xanthenium perchlorate are dissolved in 5 ml acetic acid anhydride, ca.1 ml pyridine is added and the mixture is left at RT for 2 h. Then the solvent is extracted in vacuum and the residue is purified by column chromatography (SiO$_2$, eluent toluol/ethanol in the ratio 7:1).

194 mg (47%) yield. UV/Vis (ethanol): $\lambda_{max}$ ($\epsilon$)=650 nm (80,000 I·mol$^{-1}$·cm$^{-1}$). —Fluorescence (ethanol): $\lambda_{em}$=670 nm. –MS (ESI$^\oplus$): 626 (M+H)$^\oplus$. —C$_{37}$H$_{43}$N$_3$O$_6$ (625.76).

Production of the Preliminary Products C and D

C. N-(3-hydroxypropyl)-N'-butyl urea, cf. FIG. 10:

751 mg (10.0 mmol) 3-aminopropanol is dissolved in 5 ml toluol and 991 mg (10.0 mmol) butylisocyanate is added in drops, during which process the temperature rises to about 40° C. As the mixture cools, a colorless substance precipitates out. The suspension is warmed to 70° C., until the precipitate goes back into solution. The voluminous precipitate that appears during the next cooling is taken up into about 3 ml toluol, removed by suction, washed with toluol and ether and dried in vacuum. 1.57 g (90%) yield. —$^1$H NMR (250 MHz, CDCl$_3$): 0.92 (t, 3H), 1.36 (m, 2H), 1.46 (m, 2H), 1.65 (m, 2H), 3.14 (dt, 2H), 3.32 (dt, 2H), 3.65 (dt, 2H), 4.21 (t, 1H), 5.22 (t, 1H), 5.44 (t, 1H). –MS (ESI$^\oplus$): 175 (M+H)$^\oplus$. —C$_8$H$_{18}$N$_2$O$_2$ (174.24).

D. 1-N-(3'-hydroxypropyl)-3-N'-butyl-2,4,6-trioxo-5H-pyrimidine, cf. FIG. 11:

1011 mg (5.8 mmol) N-3-hydroxypropyl-N'-butyl urea and 624 mg (6.0 mmol) malonic acid are dissolved in 4 ml acetic acid and warmed to 60° C. Then 8 ml acetic acid anhydride is slowly dripped into this solution, which is subsequently kept for 6 h at 100° C. After cooling to room temperature the solvent is extracted in vacuum. The remaining oily residue is dried in high vacuum and used for dye synthesis without further purification. 1.42 g (86%) raw yield.

Exemplary Embodiments 8-17 (compounds with the general formula II)

8. 1-butyl-5-{2-[3-(methyl)-4-(phenyl)-7-(diethylamino)-2H-2-chromenylidene]ethylidene}-3-(3-hydroxypropyl)hexahydro-2,4,6-pyrimidine trione (F 45), cf. FIG. 12:

261 mg (0.60 mmol) 3-(methyl)-4-(phenyl)-7-(diethylamino)-2-[(E)-2-methoxy-1-ethenyl]-chromenium tetrafluoroborate and 171 mg (0.60 mmol) 1-N-(3'-hydroxypropyl)-3-N'-butyl-2,4,6-trioxo-5H-pyrimidine are dissolved in 20 ml ethanol, ca. 1 ml triethylamine is added and the mixture is warmed briefly to about 70° C. After cooling to room temperature it is left for 30 minutes; then the solvent is extracted in vacuum and the residue chromatographed (SiO$_2$, eluent toluol/ethanol in the ratio 7:3).

110 mg (33%) yield. UV/Vis (ethanol): $\lambda_{max}$ ($\epsilon$)=622 nm (92,000 I·mol$^{-1}$·cm$^{-1}$). —Fluorescence (ethanol): $\lambda_{em}$=654 nm. –$^1$H NMR (400 MHz, CDCl$_3$): some signals appear doubly (regioisomerism with respect to hydroxypropyl group) 0.93/0.95 (t, 3H), 1.18/1.20 (t, 6H), 1.38 (m, 2H), 1.62 (m, 2H), 1.88 (m, 2H), 1.96/1.98 (s, 3H), 3.42/3.43 (q, 4H), 3.54 (m, 2H), 3.95 (m, 2H), 4.14 (m, 2H), 6.50 (d, 1H), 6.67 (d, 1H), 6.80 (d, 1H), 7.18 (d, 2H), 7.47 (m, 3H), 7.64/7.66 (d, 1H), 8.96/8.98 (d, 1H). –MS (ESI$^-$): 558 (M+H)$^-$. —C$_{33}$H$_{39}$N$_3$O$_5$ (557.69).

9. Preparation of the Phosphoramidite of F 45 with 2-cyanoethyl-bis-N,N,N'-tetraisopropyl phosphoramidite, cf. FIG. 13:

50 mg (0.09 mmol) F 45 and 36 mg (0.12 mmol) 2-cyanoethyl-bis-N,N,N',N'-tetraisopropyl phosphoramidite are dissolved in dry dichloromethane. The condensation reaction is started by adding 1.4 mg (0.02 mmol) tetrazole, after which the mixture is stirred for 2 hours. After the reaction has ended, the solvent is extracted in vacuum, the remaining solid is washed 3 times with 15 ml diethylether each time, and is dried in a high vacuum. This reaction proceeds quantitatively.

10. 1,3-dibutyl-5-{2-[2-(tert-butyl)-7-(diethylamino)-4H-4-chromenylidene]ethylidene}-hexahydro-2,4,6-pyrimidine trione (F 34), cf. FIG. 14:

241 mg (0.60 mmol) 2-(tert-butyl)-7-(diethylamino)-4 [(E)-2-methoxy-1-ethenyl]-chromenium-tetrafluoroborate and 144 mg (0.60 mmol) 1-N,3-N'-dibutyl-2,4,6-trioxo-5H-pyrimidine are dissolved in 5 ml acetic acid anhydride, ca.1 ml pyridine is added and the mixture is left at RT for 2 h. Subsequently the solvent is extracted in vacuum and the residue purified by column chromatography (SiO$_2$, eluent toluol/ethanol in the ratio 7:1).

175 mg (56%) yield. UV/Vis (ethanol): $\lambda_{max}$ ($\epsilon$)=557 nm (152,600 I·mol$^-{}_1$·cm$^{-1}$). —Fluorescence (ethanol): $\lambda_{em}$=576 nm. –$^1$H NMR (250 MHz, CDCl$_3$): 0.92 (t 3H), 0.93 (t, 3H), 1.22 (t, 6H), 1.34 (s, 9H), 1.35 (m, 4H), 1.62 (m, 4H), 3.42 (q, 4H), 3.94 (t, 4H), 6.40 (s,1H), 6.70 (dd,1H), 6.93 (s,1H), 8.02 (d, 1H), 8.29 (d, 1H), 8.67 (d, 1H). $^{13}$C NMR (62 MHz, CDCl$_3$): 12.53, 13.83, 13.85, 20.30, 20.35, 28.13, 30.41, 30.48, 36.59, 40.84, 41.47, 44.84, 96.53, 98.80, 102.89, 107.46, 110.57, 111.68, 126.94, 148.96, 151.83, 151.89, 152.05, 156.61, 163.10, 164.02, 169.59. –MS (ESI$^\oplus$): 522 (M+H)$^\oplus$, 1043 (2M+H)$^\oplus$. —C$_{31}$H$_{43}$N$_3$O$_4$ (521.70).

11. Sodium Salt of 3-[5-{2-[2-(tert-butyl)-7-(diethylamino)-4H-4-chromenyl idene]ethylidene}-3-(5-carboxypentyl)-2,4,6-trioxohexahydro-1-pyrimidinyl]-1-propane sulfonate (F 37/DY-550), cf. FIG. 15:

Variant A 241 mg (0.60 mmol) 2-(tert-butyl)-7-(diethylamino)-4-[(E)-2-methoxy-1-ethenyl]-chromenium-tetrafluoroborate and 249 mg (0.60 mmol) 1-N-(5'-ethoxycarbonyl)-pentyl-3-N'-3'-sulfonatopropyl-2,4,6-trioxo-5H-pyrimidine are dissolved in 20 ml ethanol, ca. 1 ml triethylamine is added and the mixture is warmed briefly to about 70° C. After cooling to room temperature it is left for 30 minutes, then the solvent is extracted in vacuum and the residue chromatographed (SiO$_2$, eluent toluol/ethanol in the ratio 7:3).

The isolated ester is boiled for 2 hours with reflux in a mixture of 10 ml acetone and 10 ml 2 M hydrochloric acid, the cooled reaction solution is neutralized with NaHCO$_3$ and the solvent is extracted in vacuum. The methanol-soluble residue is again chromatographed (SiO$_2$, RP 18 eluent methanol/water in the ratio 6:4).

182 mg (45%) yield. –UV/Vis (ethanol): $\lambda_{max}$ ($\epsilon$)=557 nm (122,300 I·mol$^{-1}$·cm$^{-1}$). —Fluorescence (ethanol): $\lambda_{em}$=578 nm. –MS (ESI$^\ominus$): 644 (M$^\ominus$), 322 (M–H)$^{2\ominus}$. -C$_{32}$H$_{42}$NaN$_3$O$_9$S (667.74).

Variant B 216 mg (0.60 mmol):2-(tert-butyl)-7-(diethylamino)-4-methylchromenium-tetrafluoroborate and 274 mg (0.60 mmol) sodium salt of 1-N-(5'-ethoxycarbonyl)-pentyl-5-(methoxymethylene)-3-N'-3'-sulfonatopropyl-2,4,6-trioxohexahydro-1-pyrimidine are dissolved in 20 ml ethanol, ca. 1 ml triethylamine is added and the mixture is warmed briefly to about 70° C. The reaction solution is processed further as for Variant A.

Variant C 216 mg (0.60 mmol) 2-(tert-butyl)-7-(diethylamino)-4-methylchromenium-tetrafluoroborate, 249 mg (0.60 mmol) sodium salt of 1-N-(5'-ethoxycarbonyl)-pentyl-3-N'-3'-sulfonatopropyl-2,4,6-trioxo-5H-pyrimidine, 1 ml trimethoxy methane and 1 ml pyridine are dissolved in 10 ml acetic acid anhydride and the mixture is heated for 1 hour with reflux. The reaction solution is processed further as for Variant A.

12. Preparation of the NHS Ester of F 37 with N-hydroxysuccinimide (NHS)/N,N'-dicyclohexylcarbodiimide (DCC), cf. FIG. 16:

15 mg F 37, 14 mg DCC and 4 mg NHS are dissolved in 1 ml dry DMF. To this 10 μl triethylamine is added. Then the reaction mixture is stirred at room temperature for 24 hours and subsequently filtered. Thereafter the solvent is extracted and the residue washed with ether. This reaction proceeds quantitatively.

13. Disodium Salt of 3-[5-(2-{2-tert-butyl-7-[ethyl-(3-sulfonatopropyl)-amino]-4H-4-chromenylidene}-ethylidene)-3-(5-carboxypentyl)-2,4,6-trioxohexahydro-1-pyrimidinyl]-1-propane sulfonate (V03-01173), cf. FIG. 17:

219 mg (0.60 mmol) 2-tert-butyl-7-[ethyl-(3-sulfonatopropyl)-amino]-4-methylchromenium (Betain) and 274 mg (0.60 mmol) sodium salt of 1-N-(5'-ethoxycarbonyl)pentyl-5-(methoxymethylene)-3-N'-3'-sulfonatopropyl-2,4,6-trioxohexahydro-1-pyrimidine are dissolved in 20 ml methanol, ca. 1 ml triethylamine is added and the mixture is heated briefly until simmering. The reaction solution is processed further as for exemplary embodiment 11, Variant A.

165 mg (35%) yield. UV/Vis (ethanol): $\lambda_{max}$ ($\epsilon$)=556 nm (142,000 I·mol$^{-1}$·cm$^{-1}$). —Fluorescence (ethanol): $\lambda_{em}$=580 nm. –MS (ESI$^\ominus$): 369 (M)$^{2\oplus}$. —C$_{33}$H$_{43}$Na$_2$N$_3$O$_{12}$S$_2$ (783.80).

14. Sodium Salt of 3-[5-{(E)-4-[2-(tert-butyl)-7-(diethylamino)-4H-4-chromenylidene]-2-butenylidene}-3-(5-carboxypentyl)-2,4,6-trioxohexahydro-1-pyrimidinyl]-1-propane sulfonate (F 38), cf. FIG. 18:

318 mg (0.60 mmol) N-1-{(1E,3E)-4-[2-(tert-butyl)-7-(diethylamino)-4-chromeniumyl -1,3-butadienyl}-N-1-phenylacetamide tetrafluoroborate and 249 mg (0.60 mmol) sodium salt of 1-N-5'-(ethoxycarbonyl)-pentyl-3-N'-3'-sulfonatopropyl-2,4,6-trioxo-5H-pyrimidine are brought to reaction and processed further as for exemplary embodiment 11, Variant A.

148 mg (36%) yield. UV/Vis (ethanol): $\lambda_{max}$ ($\epsilon$)=655 nm (145,000 I·mol$^{-1}$·cm$^{-1}$). —Fluorescence (ethanol): $\lambda_{em}$=678 nm. –$^1$H NMR (250 MHz, D$_2$O): 0.97 (t, 6H), 1.15 (s, 9H), 1.23 (m, 2H), 1.48 (m, 4H), 1.89 (m, 2H), 2.12 (m, 2H), 2.83 (t, 2H), 3.15 (s, br, 4H), 3.59 (s, br, 2H), 3.74 (s, br, 2H), 5.93 (d, 1H), 6.06 (s, 1H), 6.15 (s, 1H), 6.55 (d, 1H), 6.81 (m, 1H), 6.95 (m, 2H), 7.19 (d, 1H). –MS (ESI$^\ominus$): 670 (M$^\ominus$), 335 (M–H)$^{2\ominus}$.—C$_{34}$H$_{44}$NaN$_3$O$_9$S (693.78).

15. Sodium Salt of 3-[5-{2-[2-(tert-butyl)-9-ethyl-6,8,8-trimethyl-8,9-dihydro-4H-pyrano-[3,2-g]quinolin-4-ylidene]ethylidene}-3-(5-carboxypentyl)-2,4,6-trioxo-hexahydro-1-pyrimidinyl]-1-propane sulfonate (F 48), cf. FIG. 19:

272 mg (0.60 mmol) 2-(tert-butyl)-9-ethyl-4-[(E)-2-methoxy-1-ethenyl]-6,8,8-trimethyl-8H,9H-pyrano[3,2-g]quinolin-1-ium-tetrafluoroborate and 249 mg (0.60 mmol) sodium salt of 1-N-(5'-ethoxycarbonyl)-pentyl-3-N'-3'-sulfonato-propyl-2,4,6-trioxo-5H-pyrimidine are brought to reaction and processed as for exemplary embodiment 11, Variant A.

180 mg (42%) yield. UV/Vis (ethanol): $\lambda_{max}$ ($\epsilon$)=574 nm (132,000 I·mol$^{-1}$·cm$^{-1}$). —Fluorescence (ethanol): $\lambda_{em}$=605 nm. –MS (ESI$^{\ominus}$): 696 (M$^{\ominus}$), 348 (M–H)$^{2\ominus}$. —$C_{36}H_{46}NaN_3O_9S$ (719.82).

16. Sodium Salt of 3-[5-{4-[2-(tert-butyl)-9-ethyl-6,8,8-trimethyl -8,9-dihydro-4H-pyrano-[3,2-g]quinolin-4-ylidene]-2-butenylidene}-3-(5-carboxypentyl)-2,4,6-trioxo-hexahydro-1-pyrimidinyl]-1-propane sulfonate (F 50), cf. FIG. 20:

350 mg (0.60 mmol) N-1-{(1E,3E)-4-[2-(tert-butyl)-9-ethyl-6,8,8-trimethyl-8H,9H-pyrano-[3,2g]quinolin-1-ium-4-yl]-1,3-butadienyl}-N-1-phenylacetamide tetrafluoroborate and 249 mg (0.60 mmol) sodium salt of 1-N-(5'-ethoxycarbonyl)-pentyl-3-N'-3'-sulfonatopropyl-2,4,6-trioxo-5H-pyrimidine are brought to reaction and processed as for exemplary embodiment 11, Variant A. 144 mg (32%) yield.-UV/Vis (ethanol): $\lambda_{max}$ ($\epsilon$)=671 nm (175,000 I·mol$^{-1}$·cm$^{-1}$). —Fluorescence (ethanol): $\lambda_{em}$=700 nm. –MS (ESI$^{\ominus}$): 722 (M$^{\ominus}$), 361 (M–H)$^{2\ominus}$. —$C_{38}H_{48}NaN_3O_9S$ (745.86).

17. Preparation of the NHS Ester of F 50 with N-hydroxysuccinimide (NHS)/N,N'-dicyclohexylcarbodiimide (DCC), cf. FIG. 21:

15 mg F 50, 14 mg DCC and 4 mg NHS are dissolved in 1 ml dry N,N-dimethylformamide (DMF). To this is added 10 μl triethylamine. Next the reaction mixture is stirred for 24 hours at room temperature and then filtered. Susequently the solvent is extracted and the residue washed with ether. This reaction proceeds quantitatively.

18. Absorption and Emission Spectrum of a DY-610-DNA Conjugate, cf. FIG. 22:

The F-39-NHS ester (exemplary embodiment 2, FIG. 4) (0.2 mg in 200 μl DMF) is converted in borate buffer (0.1 M, pH 8.5) with a 5'-aminomodified DNA oligomer (23 mer), while being shaken overnight at 37° C. Subsequently 2.1 ml distilled water is added to the reaction mixture. The entire volume is now put into a NAP25 column (Amersham Pharmacia) and eluted with 3.5 ml water. The collected eluate is then dried in vacuum. The HPLC purification of the conjugate is done on a RESOURCE™ RPC column (Amersham Pharmacia) with triethylammonium acetate (100 mM, pH 6.9) and triethylammonium acetate (100 mM, pH 6.9)/acetonitrile (1:1) as eluents.

The absorption spectrum was taken on a Lambda16 Spectrophotometer (Perkin-Elmer) in distilled water. The fluorescence spectrum was recorded on an Aminco-Bowman 2 fluorimeter (excitation wavelength 550 nm, column 4/4). Both spectra, normalized to the longest-wavelength absorption maximum and the emission maximum, respectively, are shown in FIG. 22.

19. Labeling of Avidin with DY-550-NHS ester, cf. FIG. 23:

0.49 mg (641 nmol) DY-550-NHS ester (exemplary embodiment 12, FIG. 16) is dissolved in 106 μl N,N-dimethylformamide (DMF). Likewise, 1 mg avidin (15.15 nmol) is dissolved in 200 μl bicarbonate buffer (pH 9.0, 50 mM). Then 5 μl of the DY-550-NHS-ester solution is pipetted into the avidin solution. Now this initial labeling mixture is left in the dark for one hour at room temperature, during which time it is occasionally shaken. Thereafter, the resulting DY-550-avidin conjugte is run through a Sephadex column (Sephadex G 25 medium) to separate it from unreacted or hydrolyzed NHS ester, using phosphate buffer (pH 7.2, 22 mM, 0.1% azide) as eluent. Having been thus purified, the DY-550-avidin-conjugate solution is filled up to 1 ml (likewise with phosphate buffer, pH 7.2, 22 mM) and characterized by recording an absorption and a fluorescence spectrum. For this purpose the conjugate solution is diluted to one-tenth with the above-mentioned phosphate buffer and measured in a 1-cm quartz cuvette (open on four sides) with the absorption spectrometer Lambda 16 (Perkin-Elmer) and the fluorescence spectrometer Aminco-Bowman 2 (column 4/4, PMT voltage 700 V). FIG. 23 shows the spectra so obtained, normalized to the absorption and emission, respectively, maxima of the dye.

What we claim is:

1. A compound of the formula I or II

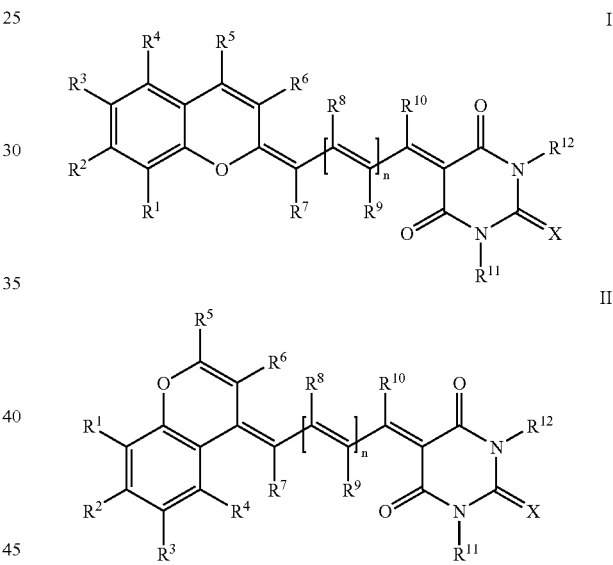

wherein
(a) $R^1$ and $R^3$ to $R^{12}$ may each be the same or different and is selected from the group consisting of hydrogen, chlorine, bromine, and a substituent selected from the group consisting of an alkyl, aryl, heteroaryl, cycloalkyl, heterocycloalkyl, alkyloxy, alkylmercapto, aryloxy, arylmercapto, heteroaryloxy, heretoarylmercapto, cyano, an isocyano, isothiocyano, hydrazino, amino, monochloro- and dichloro- or monobromo- and dibromo-triazinyl, aziridino, sulfonyl halogenid, N-hydroxysuccinyl, imido, glyoxyl, maleimido, iodacetamido, and phosphoramido; and wherein the substituent may also contain, apart from carbon and hydrogen, as many as 4 oxygen atoms and 0, 1 or 2 nitrogen atoms, or one sulfur atom, or one sulfur and one nitrogen atom;
(b) $R^1$ and $R^2$, $R^2$ and $R^3$, $R^3$ and $R^4$, $R^5$ and $R^6$, and $R^6$ and $R^7$ together may form an aromatic, non-aromatic or nitrogen-containing 5- or 6-member ring;
(c) X represents oxygen or sulfur;
(d) n is zero, 1, 2 or 3;

(e) and with the proviso that $R^2$ must contain a nitrogen atom and is a substituted or unsubstituted amino group or a nitrogen-containing 5- or 6- membered ring.

2. A compound as claimed in claim 1 wherein each of the residues $R^1$ and $R^3$ to $R^{12}$ have at most 10 carbon atoms.

3. A compound as claimed in claim 1 wherein not more than four of the residues $R^1$ and $R^3$ to $R^{12}$ contain a sulfur atom.

4. A compound as claimed in claim 1 wherein said groups $R^1$ and $R^3$ to $R^{12}$ contain from 1 to 6 carbon atoms.

5. A compound as claimed in claim 1, wherein X represents oxygen.

6. A compound as claimed in claim 1, wherein n represents zero, 1 or 2.

* * * * *